United States Patent [19]

Dahlberg et al.

[11] Patent Number: 5,395,765
[45] Date of Patent: Mar. 7, 1995

[54] **THERMOSTABLE XYLANASE FROM A STRAIN OF *RHODOTHERMUS MARINUS***

[75] Inventors: Leif A. L. Dahlberg, Löddeköpinge; Olof P. Holst, Harlösa, both of Sweden; Lisbeth Anker, Copenhagen, Denmark

[73] Assignee: Novo Nordisk A/S, Bagsvaerd, Denmark

[21] Appl. No.: 211,142

[22] PCT Filed: Oct. 14, 1992

[86] PCT No.: PCT/DK92/00300

§ 371 Date: Mar. 22, 1994

§ 102(e) Date: Mar. 22, 1994

[87] PCT Pub. No.: WO93/08275

PCT Pub. Date: Apr. 29, 1993

[30] Foreign Application Priority Data

Oct. 18, 1991 [DK] Denmark .................. 1753/91

[51] Int. Cl.$^6$ .................. D21C 1/00; D21C 3/00; C12N 9/24
[52] U.S. Cl. .................. 435/277; 435/278; 435/200
[58] Field of Search .................. 435/278, 200, 277

[56] References Cited

U.S. PATENT DOCUMENTS 4,966,850 10/1990 Yu et al. .................. 435/200

FOREIGN PATENT DOCUMENTS 57-146576 9/1982 Japan .
WO91/02839 3/1991 WIPO .

OTHER PUBLICATIONS

Eriksson et al., Wood Sci. Technol., 14: 267–279, 1980.
Abstract of Japanese Patent No. JP 60-58070 published Apr. 4, 1985.
Alfredsson et al., J. of Gen. Microbiology, vol. 134, pp. 299–306.
Detroy R. W., Organic Chemicals from Biomass, pp. 19–41 (1981).
Paice et al., J. Wood Chem., Technol., vol. 4, No. 2, pp. 187–198 (1984).
Pommier et al., Tappi Journal, pp. 187–191 (1989).
Paice et al., Biotech. & Bioengineering, vol. 32, pp. 235–239 (1988).
Chen et al., Biotech. Letters, vol. 10, No. 12, pp. 913–918 (1988).
Takahashi et al., Wood Sci. Technol., vol. 22, pp. 177–189 (1988).
Eriksson et al., Wood Sci. Technol., vol. 24, pp. 79–101 (1990).
Viikari et al., Proceedings 3rd Int'l Symposium on Biotech in Pulp & Paper Industry, pp. 67–69 (1986).

*Primary Examiner*—David M. Naff
*Assistant Examiner*—Mike Meller
*Attorney, Agent, or Firm*—Steve T. Zelson; Karen A. Lowney

[57] ABSTRACT

A xylanase obtained from Rhodothermus marinus, the method of obtaining it and a process for its use are disclosed. The xylanase has an optimum temperature of from 85° to 100° C., a relative activity of more than 50% in the interval of from pH 5 tp pH 8 after incubation for 5 minutes at 65° C., a relative temperature stability at 80° C. of more than 80% after incubation at pH 7 for 3 hours, a pH optimum of about 6 and an isoelectric point in the range of from 3 to 7. The xylanase can be obtained from the strains ATCC 43812, ATCC 43813 or a mutant thereof. The process for obtaining the xylanase involves cultivation of a xylanase-producing strain of Rhodothermus marinus in a suitable nutrient medium containing carbon and nitrogen sources and inorganic salts followed by recovery of the xylanase. Also disclosed is a process for the treatment of lignocellulosic pulp with the xylanase.

7 Claims, 4 Drawing Sheets

THERMOSTABLE XYLANASE FROM A STRAIN OF RHODOTHERMUS MARINUS

This application is a continuation of PCT/DK92/00300 filed Oct. 14, 1992, the contents of which are incorporated herein by reference.

TECHNICAL FIELD

This invention relates to novel enzymes. More specifically, the invention provides novel xylanases obtainable from strains belonging to the genus Rhodothermus. The invention also relates to the use of the xylanases in the treatment of lignocellulosic pulp.

BACKGROUND ART

Xylan, a major component of plant hemicellulose, is a polymer of D-xylose linked by beta-1,4-xyiosidic bonds. Xylan can be degraded to xylose and xylo-oligomers by acid or enzymatic hydrolysis. Enzymatic hydrolysis of xylan produces free sugars without the by-products formed with acid (e.g. furans).

Major applications for xylanases are enzymatic breakdown of agricultural wastes for production of alcohol fuels, enzymatic treatment of animal feeds to release free pentose sugars, manufacturing of dissolving pulps yielding cellulose, and bio-bleaching of wood pulp [Detroyrn R. W. In: *Organic Chemicals from Biomass*, (CRC Press, Boca Raton, Fla., 1981) 19–41.; Paice, M. G., and L. Jurasek., *J. Wood Chem. Technol.* 4:187-198.; Pommier, J. C., J. L. Fuentes, G. Gorna., *Tappi Journal* (1989):187-191.; Senior, D. J., et al., Biotechnol. Letters 10 (1988):907-912].

The pulp and paper industry is using xylanase compositions in the bleaching process to enhance the brightness of bleached pulps, to decrease the amount of chlorine used in the bleaching stages, and to increase the freeness of pulps in the recycled paper process [Eriksson, K. E. L., *Wood Science and Technology* 24 (1990);79-101.; Paice, M. G., R. Bemier, and L. Jurasek, *Biotechnol. and Bioeng.* 32 (1988):235-239.; Pommier, J. C., J. L. Fuentes, and G. Gorna, *Tappi Journal* (1989):187-191].

Kraft pulping, a process widely used in the pulp and paper industry, involves the alkaline sulfate cooking of pulp to remove 95% of the lignin. The remaining 5% of lignin gives the pulp a dark brown colour which has the tendency to darken in UV light or by oxidation. In order to obtain a white pulp for high quality paper, the brown colour is removed by a multi-stage bleaching process using chlorine and/or chlorine dioxide.

Presently, there is much concern about the environmental impact of the chemicals generated from the bleaching process. Enzymes can aid in the removal of lignin from the pulp without any harmful side products. Reports show that lignin in wood is linked to xylan [Eriksson, O., et al., *Wood Sci.Technol.* 14 (1980);267.; Takashi, N., and T. Koshijiima, *Wood Sci.Technol.* 22 (1988);177-189]. By a limited hydrolysis of the xylan a greater release of lignin occurs during bleaching. Thus, by enzymatically treating the pulp prior to bleaching the amount of active chlorine needed would in turn decrease [Viikari, L., et al., *Proceedings of the 3rd International Symposium on Biotechnology in the Pulp and Paper Industry* (1986);67].

SUMMARY OF THE INVENTION

Recently novel thermophilic bacteria named Rhodothermus have been isolated from an alkaline hot spring in Iceland [Alfredsson, G. A.; Kristjansson, J. K.; Hjörleifsdottir, S.; Stetter, K. O. (1988): Rhodothermus marinus, gen.nov., sp.nov., a thermophilic, halophilic bacterium from submarine hot springs in Iceland; J. Gen. Microbiol. 134; 299–306]. We have now found that these bacteria produce highly thermostable xylanolytic enzymes with good stability in a broad pH range.

Accordingly, in its first aspect, the invention provides xylanases having activity at temperatures of from below 60° to above 100° C., a relative activity of more than 50% in the interval of from pH 5 to pH 8 after incubation for 5 minutes at 65° C., a relative temperature stability at 80° C. of more than 80% after incubation at pH 7 for 3 hours, being capable of hydrolysing birchwood xylans, and having immunochemical properties identical or partially identical to those of a xylanase derived from the strain ATCC 43812, or the strain ATCC 43813, or the strain DSM 4252.

In another aspect, the invention provides a process for the preparation of a xylanase of the invention, which process comprises cultivation of a xylanase producing strain of the genus Rhodothermus in a suitable nutrient medium, containing carbon and nitrogen sources and inorganic salts, followed by recovery of the desired enzyme.

in a further aspect, the invention provides a process for treatment of lignocellulosic pulp, in which the lignocellulosic pulp is treated with an enzyme of the invention.

BRIEF DESCRIPTION OF DRAWINGS

The present invention is further illustrated by reference to the accompanying drawings, in which.

DETAILED DISCLOSURE OF THE INVENTION

The Organism

*Rhodothermus marinus*, representative of the genus Rhodothermus, is a thermophilic bacterial strain that can be isolated in submarine alkaline hot springs in Iceland. This organism is aerobic, heterotroph, gram-negative, rod-shaped and non-motile. The strain is red-pigmented, salt dependent for growth and exhibits extracellular xylanase activity.

Two strains representative for *Rhodothermus marinus* have been deposited as type cultures and hence are publicly available from Deutche Sammlung von Mikroorganismen und Zellkulturen GmbH, Mascheroder Weg 1b, D-3300 Braunschweig, Germany, under the accession number DSM 4252, and/or from American Type Culture Collection, 12301 Parklawn Drive, Rockville, Md. 20852, USA, under the accession Nos. ATCC 43812 and ATCC 43813. The deposit ATCC 43812 is stated as being identical to the deposit DSM 4252.

The organisms are able to grow on agar plates and in liquid medium with the appropriate supplementation, e.g. a medium as described in Example 1. Extracellular xylanase activity can be induced by xylan. The choice of culture system greatly affects the specific growth rate, and growth in complex or synthetic media also affects the productivity.

The Enzymes

The xylanases of this invention are obtainable from members of the genus Rhodothermus, and they may be produced by cultivation of a strain belonging to the genus Rhodothermus, preferably a strain of *Rhodothermus marinus*, most preferred the strains ATCC 43813 and ATCC 43812, the latter being identical to the strain DSM 4252, or mutants or variants thereof, in a suitable nutrient medium, containing carbon and nitrogen sources and inorganic salts, followed by recovery of the desired enzyme. The enzyme can also be obtained by recombinant DNA-technology.

The xylanase of the invention can be described by the following characteristics.

Physical-Chemical Properties

Figure 2:
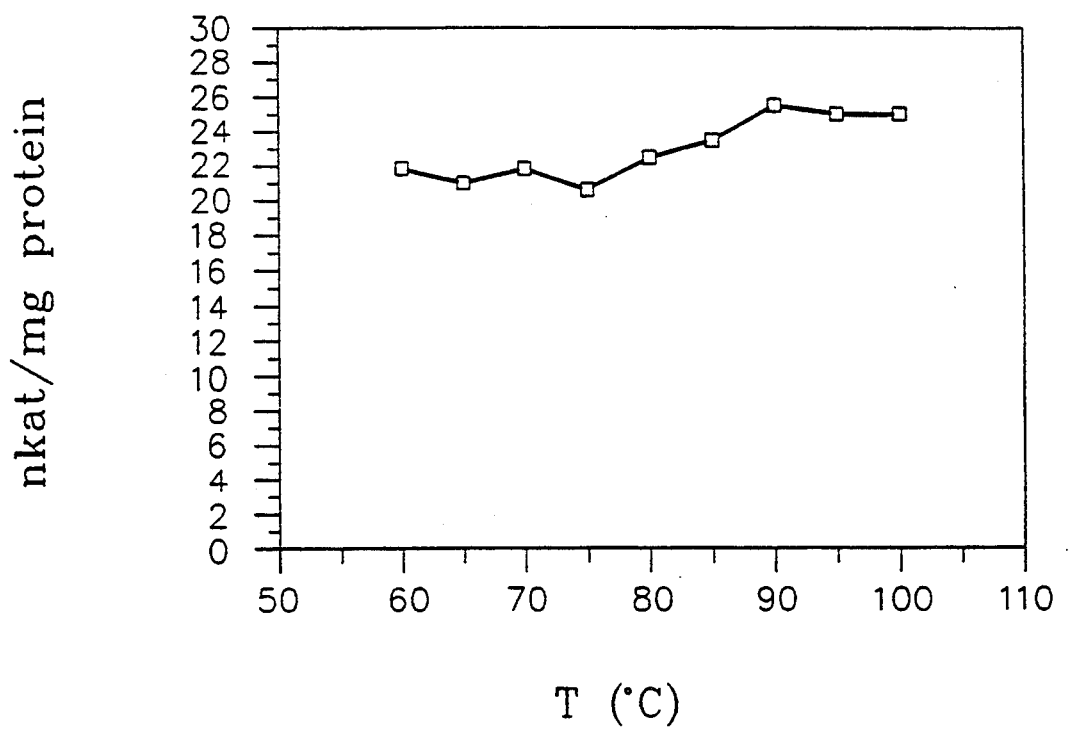
FIG. 2 illustrates the temperature optimum of a xylanase of the invention, presented as specific xylanase activity vs. different 5 min. incubation temperatures, and pH 7.

The enzyme of the invention possesses xylanolytic activity at temperatures of from below 60° to above 100° C. No pronounced temperature optimum has been detected, but apparently (cf. FIG. 2) the enzyme possesses optimum activity within a broad temperature range of from 80° C. to above 100° C., more specifically the range of from 85° C. to 100° C.

The enzyme of the invention has a relative activity of more than 50% in the interval of from pH 5 to pH 8 after incubation for 15 minutes at 65° C. Moreover, it appears (cf. FIG. 4) that the pH optimum of the enzyme is in the range of from pH 5 to 7, more specifically around pH 6, as measured after incubation for 5 minutes at 65° C. In the interval of from pH 5 to pH 8 the enzyme of the invention possesses a relative xylanolytic activity of more than 50%, as evidenced in FIG. 4.

The enzyme of the invention has a relative residual activity (temperature stability) after 3 hours of incubation, preferably 5 hours of incubation, at pH 7 and 80° C. of more than 80%. After 3 hours of incubation, preferably 5 hours of incubation, at pH 7 and 90° C., the enzyme of the invention has a relative residual activity of more than 60%. After 3 hours of incubation, preferably 5 hours of incubation, at pH 7 and 100° C., the enzyme of the invention has a relative residual activity of more than 40%.

After 24 hours of incubation at pH 7 and 80° C. a relative residual activity of more than 60% is detectable. After 24 hours of incubation at pH 7 and 90° C. a relative residual activity of more than 40% is detectable. After 24 hours of incubation at pH 7 and 100° C. a relative residual activity of more than 30% is detectable.

The enzyme of the invention has a half-life of activity ($T_{1/2}$) of approximately 3 hours of boiling (100° C.), and at 90° C. the half-life can be estimated to approximately 24 hours.

The enzyme of the invention possesses an excellent pH stability in a very broad pH interval, namely of from below pH 5 to approximately pH 12, when measured after incubation for as long as 8 hours at 65° C. The enzyme of the invention has more than half of its relative activity in the interval of from pH 5 to pH 10 after incubation at 65° C. for 4 hours.

The enzyme of the invention is capable of hydrolysing birchwood xylans as well as oatspelt and larchwood xylans.

Immunochemical Properties

The xylanases of the invention have immunochemical properties identical or partially identical (i.e. at least partially identical) to those of a xylanase derived from the strain ATCC 43812 or the strain ATCC 43813 or the strain DSM 4252.

The immunochemical properties can be determined immunologically by cross-reaction identity tests. The identity tests can be performed by the well-known Ouchterlony double immunodiffusion procedure or by tandem crossed immunoelectrophoresis according to Axelsen N. H.; Handbook of Immunoprecipitation-in-Gel Techniques; Blackwell Scientific Publications (1983), Chapters 5 and 14. The terms "antigenic identity" and "partial antigenic identity" are described in the same book, Chapters 5, 19, and 20.

Industrial Applications

Due to the excellent thermo- and pH-stability, the enzymes of this invention are well suited for a variety of industrial applications, including the four major applications for xylanases mentioned earlier in this specification. The enzymes are especially well suited for treatment of lignocellulosic pulp. Therefore, in a further aspect, the invention relates to the use of the xylanases for treatment of lignocellulosic pulp.

Enzymatic treatment of lignocellulosic pulp improves the bleachability of the pulp and/or reduces the amount of active chlorine necessary for obtaining a satisfactory bleaching.

In preferred embodiments, the xylanases of this invention can be implemented in processes for treatment of lignocellulosic pulp as described in e.g. International Patent Publications WO 91/02839 and WO 92/03608.

The following examples further illustrate the present invention, and they are not intended to be in any way limiting to the scope of the invention as claimed.

EXAMPLE 1

Screening Example

For screening of the xylanases obtainable from the genus Rhodothermus batch cultivation can be accomplished on the following complex medium (a modification of Medium 162 originally described by Degryse et al. [Degryse, E., Glansdorff N., Piérard A. (1978); Arch. Microbiol. 117 189-196]:

| | |
|---|---|
| Tryptone, Difco ® | 2.5 |
| Yeast extract, Sigma ® | 2.5 |
| Base solution, pH 7.2[1] | 100 ml |
| Buffer solution, pH 7.2[2] | 100 ml |

This medium was supplemented with 2.0% NaCl and 0.5% birch xylan (Roth ® 7500).

| [1]Consisting of (g/liter): | |
|---|---|
| Nitriloacetic acid (Titriplex I) | 1.0 |
| NaOH | 0.2 |
| $CaSO_4;2H_2O$ | 0.4 |
| $MgCl_2;6H_2O$ | 2.0 |
| Fe-citrate (0.01M) | 5.0 ml |

| (2)Consisting of (g/liter): | |
| --- | --- |
| KH$_2$PO$_4$ | 5.44 |
| Na$_2$HPO$_4$;2H$_2$O | 21.40 |

All components were sterilized by autoclaving at 121° C. for 20 min. Fe-citrate was sterilized separately.

The medium can be solidified with 2.8% (w/v) agar, Difco ®.

Detection:

In order to observe extracellular xylanase activity of the colonies on agar plates, strains are streaked on solidified medium plates and incubated at 65° C. over-night. Plates are then flooded with 0.05% (w/v) aqueous solution of Congo Red for 10 minutes. After pouring off the excess of Congo Red solution, each plate is washed twice with 1M NaCl for 10 minutes.

Xylanase producing strains are detectable from the clear zone around the these colonies. The strains so obtained can be cultivated according to the method described in Example 2 in order to obtain a crude xylanase preparation.

In order to detect the activity on birchwood xylan and oatspelt xylan, respectively, 20 microlitre samples of xylanase containing culture fluid were applied in 4 mm diameter wells in agar medium plates containing the respective xylans, the plates being incubated overnight at 55° C. and the clearing zones visualized as described above.

Clearing zones were detected both on birch xylan and oatspelt xylan.

EXAMPLE 2

Cultivation Example

For preliminary studies and characterization of xylanases obtainable from Rhodothermus batch cultivation of the strain DSM 4252 was accomplished on a liquid complex medium of a composition as described in Example 1.

The strains were pre-inoculed for 20 hours in rotating shake-flasks on a glycerol bath at 65° C. 5 ml of this culture were used to inoculate 50 ml of growth medium in 500 ml baffled shake-flasks. After 18 hours at 65° C. the culture was centrifuged (on a Wifug ® centrifuge at 6000 rpm for 15 min.) and the supernatant filtrated using a 0.2µ cellulose acetate filter (Sartorius ®).

These enzyme preparations were used for characterization of the xylanases of the invention.

From similar batch cultivation experiments it was demonstrated that extracellular xylanase activity is induced by the addition of xylan.

EXAMPLE 3

Characterization Example

Assay for xylanolytic activity was performed essentially as described by Barley & Poutanen and Khan et al. [Bailey M. J, Poutanen K. (1989); Appl. Microbiol. Biotechnol. 30 5–10; and Khan A. W., Tremblay D., & Leduy Anh (1986); Enzyme Microbiol. Technol. 8 373–377].

To 1.8 ml of substrate containing 1% (w/v) birch xylan (Roth ® 7500) in a 25 mM sodiumphosphate buffer, pH 7.1, 0.2 ml of the enzyme preparation obtained according to Example 2 was added. After incubation for 5 minutes at 65° C., 3.0 ml of 3,5-dinitrosalicylic acid (DNS) were added, and the solution was boiled for 15 minutes.

After cooling down to room-temperature the amount of colour produced was measured as $A_{540\ nm}$.

Temperature Dependency

In order to examine the thermal stability of the enzyme of the invention, the enzyme preparation obtained according to Example 2 was incubated at 80° C., 90° C., and 100° C. respectively, and samples were taken at various intervals (1, 3, 5, and 24 hours). Enzymatic activity was determined by the above described method, and the results are presented in FIG. 1.

As evidenced by this Figure, the xylanase of the invention possesses a remarkable temperature stability. After 24 hours of incubation at pH 7 and 80° C. a relative residual activity of more than 60% is detectable. After 24 hours of incubation at pH 7 and 90° C. a relative residual activity of more than 40% is detectable. After 24 hours of incubation at pH 7 and 100° C. a relative residual activity of more than 30% is detectable.

Figure 1:
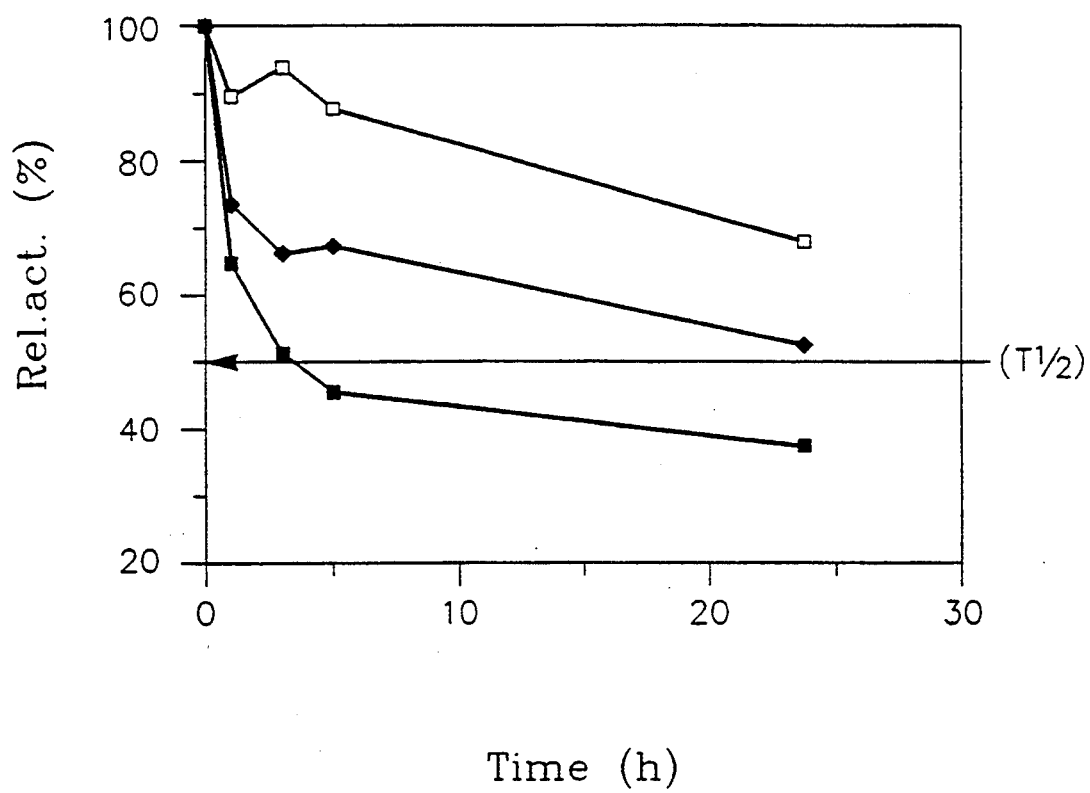
FIG. 1 illustrates the temperature stability of a xylanase of the invention, presented as % relative residual activity vs. time, at different temperatures (□80° C.; ♦ 90°C; ■ 100°C) and pH 7.

From FIG. 1 a half-life of activity ($T_{1/8}$) appears to be approximately 3 hours at 100° C., and at 90° C. the half-life can be estimated to approximately 24 hours.

In order to examine the temperature optimum of the xylanases of the invention, the enzymatic activity was determined after incubating the enzyme preparation obtained according to Example 2 at different temperatures (60°–100° C.; pH 7) for 5 minutes. These results are presented in FIG. 2.

From this Figure it appears that the enzyme of the invention possesses xylanolytic activity at temperatures of from below 60° C. to above 100° C. No pronounced temperature optimum has been detected, but apparently the enzyme possesses optimum activity within a broad range of from 80° to above 100° C., more specifically 85° to 100° C.

pH Dependency

Figure 3:
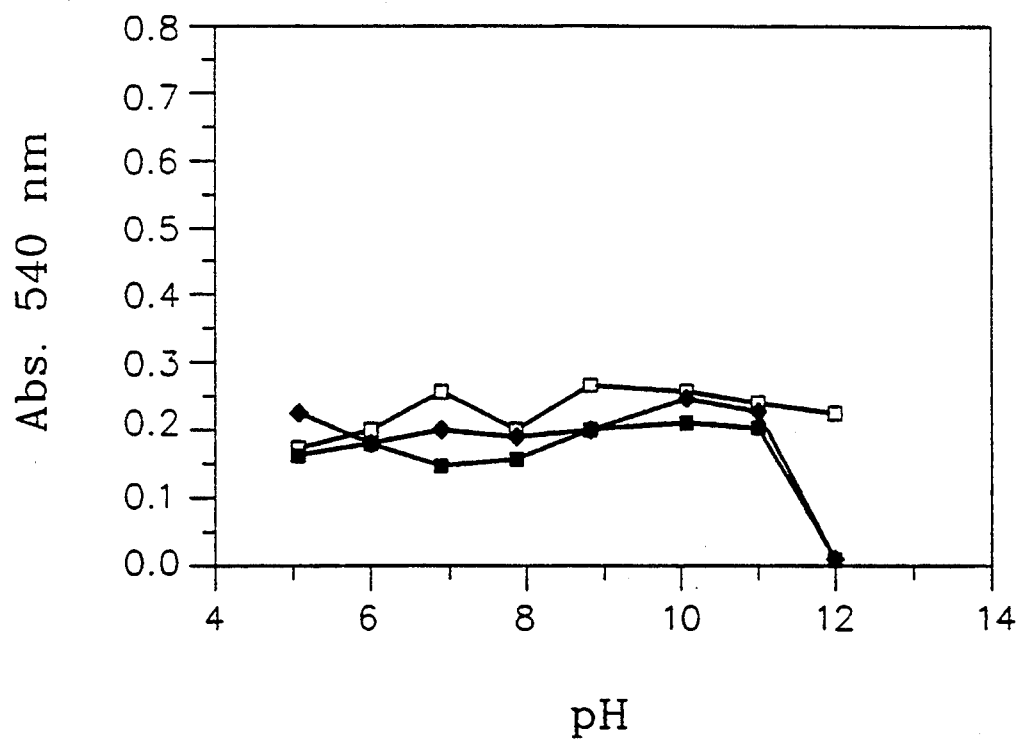
FIG. 3 illustrates the pH stability of a xylanase of the invention, presented as absorbance at 540 nm (i.e. xylanase activity) vs. different pH values, and at different incubation times (□ 0 h inc.; ♦ 4 h inc.; ■ 8 h inc.), and 65°C.

In order to examine the pH stability of the enzyme of the invention, the enzyme preparation obtained according to Example 2 was incubated at different pH values (5–12) at 65° C., and samples were taken at various intervals (0, 4, and 8 hours). The xylanolytic activity was determined by the method described above. The results are presented in FIG. 3.

From this Figure it appears that after incubation for up to 8 hours the enzyme possesses pH stability in a very broad pH interval, namely of from below pH 5 to approximately pH 11, when measured at 65° C.

In order to examine the pH optimum of the xylanases of the invention, the enzymatic activity was determined after incubation of the enzyme preparation at different pH values (4–11) at 65° C. for 5 minutes. The results are presented in FIG. 4. The activity curve shown on this figure is based on the results using the following four buffer solutions: Citrate-phosphate buffer, pH 4–7; Phosphate buffer, pH 6–8; Tris buffer, pH 7–9; and Glycine-NaOH, pH 9–11.

To avoid negative interference with the DNS, the samples were diluted with water prior to activity determination.

Figure 4:
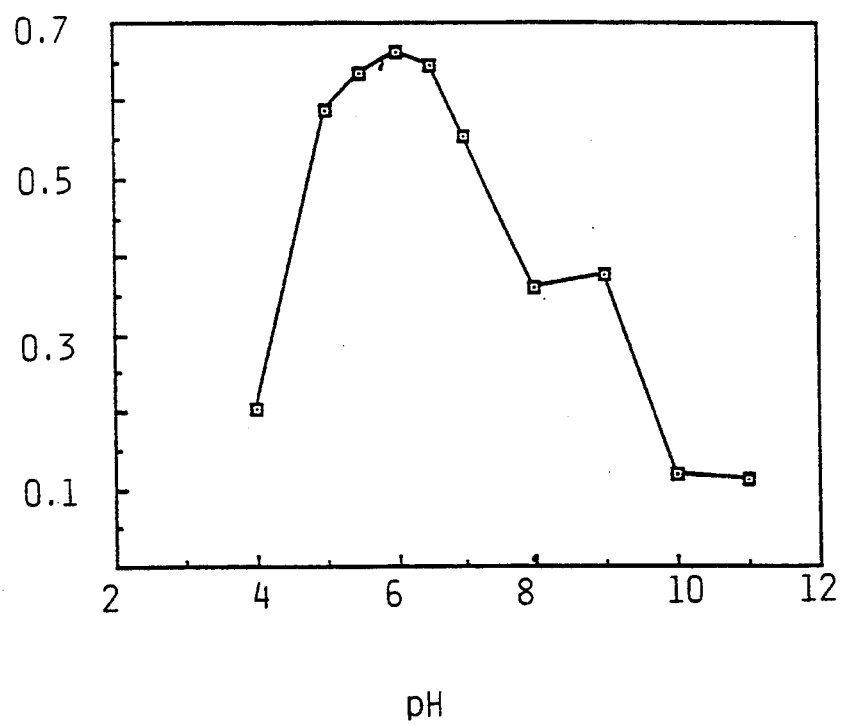
FIG. 4 illustrates the pH activity of a xylanase of the invention, after incubation for 5 min. at 65° C., presented as the absorbance at 540 nM measured at pH values 4–11.

From FIG. 4 it appears that the enzyme of the invention possesses xylanolytic activity in a range of from pH below 4 to above 11. Moreover, it appears that the pH optimum of the enzyme is in the range of from pH 5 to 7, more specifically around pH 6, as measured after incubation for 5 minutes at 65° C. In the interval of from pH 5 to pH 8 the enzyme of the invention possesses a relative xylanolytic activity of more than 50%.

pI of the Xylanase Activity

A powder xylanase preparation was made by lyophilizing the crude culture broth obtained according to Ex. 2.

The pI of the xylanase activity was determined using LKB ampholine PAG plates pH 3.5–9.5 and a solution made from the lyophilized powder xylanase preparation. After the electrophoresis the gel is washed twice for 15 minutes, once in water, once in trisbuffer pH 9, and then overlaid with a thin coat of detection agar consisting of 0.5% of birch xylan (Roth ® 7500), 1% of agarose, pH 9. The overlaid gel is incubated overnight at 50° C. The xylanase activity was visualized using Congo Red staining (staining for 10 minutes with 0.1% of Congo Red and destained for 2×15 minutes in 1M NaCl).

At least 2 components with xylanolytic activity could be detected in the range of from 3 to 7.

We claim:

1. A xylanase obtained from a strain of Rhodorhermus marinus, the xylanase having the following properties:
   (a) Optimum activity at temperatures of from 85 to 100° C.;
   (b) A relative activity of more than 50% in the interval of from pH 5 to pH 8 after incubation for 5 minutes at 65° C.;
   (c) A relative temperature stability at 80° C. of more than 80% after incubation at pH 7 for 3 hours;
   (d) a pH optimum of about 6;
   (e) a pI in the range of from 3 to 7.

2. The xylanase according to claim 1, obtained from the strain ATCC 43812, or the strain ATCC 43813, or a mutant thereof.

3. The xylanase according to claim 1, which hydrolyzes birchwood xylans.

4. A process for the preparation of a xylanase having the following properties:
   (a) Optimum activity at temperatures of from 85° to 100° C.;
   (b) A relative activity of more than 50% in the interval of from pH 5 to pH 8 after incubation for 5 minutes at 65° C.;
   (c) A relative temperature stability at 80° C. of more than 80% after incubation at pH 7 for 3 hours;
   (d) a pH optimum of about 6;
   (e) a pI in the range of from 3 to 7;
which process comprises cultivation of a xylanase-producing strain of *Rhodothermus marinus* in a suitable nutrient medium, containing carbon and nitrogen sources and inorganic salts, followed by recovery of the xylanase.

5. The process according to claim 4, in which the strain ATCC 43812, or the strain ATCC 43813, or a mutant thereof, is cultivated.

6. A process for the treatment of lignocellulosic pulp, in which the lignocellulosic pulp is treated with a xylanase obtained from *Rhodochermus marinus*, the xylanase having the following properties:
   (a) Optimum activity at temperatures of from 85° to 100° C.;
   (b) A relative activity of more than 50% in the interval of from pH 5 to pH 8 after incubation for 5 minutes at 65° C.;
   (c) A relative temperature stability at 80° C. of more than 80% after incubation at pH 7 for 3 hours;
   (d) a pH optimum of about 6;
   (e) a *in the range of from* 3 to 7.

7. The process of claim 6 in which the xylanase is obtained from strain ATCC 43812, or the strain ATCC 43813, or a mutant thereof.

* * * * *